(12) United States Patent
Barham

(10) Patent No.: US 7,164,059 B2
(45) Date of Patent: Jan. 16, 2007

(54) METHOD OF PRODUCING SEEDLESS WATERMELON

(75) Inventor: Warren S. Barham, Gilroy, CA (US)

(73) Assignee: Seminis Vegetable Seeds, Inc., Oxnard, CA (US)

( * ) Notice: Subject to any disclaimer, the term of this patent is extended or adjusted under 35 U.S.C. 154(b) by 202 days.

(21) Appl. No.: 10/422,056

(22) Filed: Apr. 23, 2003

(65) Prior Publication Data

US 2004/0073978 A1 Apr. 15, 2004
US 2006/0200880 A9 Sep. 7, 2006

Related U.S. Application Data

(60) Continuation-in-part of application No. 10/328,722, filed on Dec. 23, 2002, and a division of application No. 10/025,819, filed on Dec. 26, 2001, now abandoned.

(51) Int. Cl.
*A01H 1/00* (2006.01)
*A01H 1/02* (2006.01)
*A01H 5/00* (2006.01)

(52) U.S. Cl. .................. 800/308; 800/260; 800/298

(58) Field of Classification Search .............. 800/260, 800/266, 268, 269, 308, 298; 435/410, 418, 435/419, 421, 430, 430.1
See application file for complete search history.

(56) References Cited

U.S. PATENT DOCUMENTS

| | | | |
|---|---|---|---|
| 5,007,198 A | | 4/1991 | Gray et al. |
| 5,304,719 A | * | 4/1994 | Segebart ............... 800/303 |
| 5,367,109 A | * | 11/1994 | Segebart ............ 800/320.1 |
| 5,763,755 A | * | 6/1998 | Carlone ............. 800/320.1 |
| 5,850,009 A | * | 12/1998 | Kevern ................ 800/271 |

OTHER PUBLICATIONS

Crall et al. HortScience 29(6): 707-708 (1994).*

* cited by examiner

*Primary Examiner*—David H. Kruse
*Assistant Examiner*—Keith O. Robinson
(74) *Attorney, Agent, or Firm*—Alissa M. Eagle; David R. Marsh; Arnold & Porter LLP

(57) ABSTRACT

The present invention is a novel method which improves the economical production of seedless watermelon fruit. The novel method involves using short vine pollinators in the production field to pollinate the triploid hybrids which result in increased yields.

7 Claims, No Drawings

METHOD OF PRODUCING SEEDLESS WATERMELON

CROSS REFERENCE

This application is a divisional application of U.S. application Ser. No. 10/025,819, filed on Dec. 26, 2001, and a continuation-in-part of U.S. application Ser. No. 10/328,722, filed on Dec. 23, 2002.

BACKGROUND OF THE INVENTION

The present invention relates to a novel method of producing seedless watermelons using short vine pollinators. The present invention also relates to a watermelon seed, a watermelon plant, watermelon flower, and a watermelon variety which comprise having a short vine.

Watermelon belongs to the family Cucurbitaceae. Watermelon is commercially grown from either seed or transplants. *Citrullus* is a member of the family Cucurbitaceae. The Cucurbitaceae is a family of about 90 genera and 700 to 760 species, mostly of the tropics. The family includes pumpkins, squashes, gourds, melons, cucumber, watermelon, loofah, and several weeds. A bitter-fruited form of *Citrullus* vulgaris appears to be the ancestor of the cultivated watermelon.

Successful watermelon production depends on attention to various cultural practices. This involves soil management practices with special attention to proper fertilization, crop establishment with appropriate spacing, weed control, the introduction of bees for pollination, and suitable pollenizers for seedless watermelon, irrigation and pest management. Watermelon fruit size and shape; rind color; thickness and toughness; seed size, color and number; and flesh color, texture, soluble solids and freedom from fruit defects are all important characteristics to be considered in selection of watermelon varieties. In addition, seedless watermelons should be free of hard seeds and have undeveloped seeds that are small and innocuous.

Watermelon crops can be established in the field from seed or from transplants. Transplanting is becoming more common because transplanting usually results in earlier crops than those that are direct seeded. Transplants are used extensively to establish seedless watermelon plantings. Diploid and triploid watermelon crops can be established easily with high quality transplants. Transplanting helps achieve rapid, complete plant stands, especially where seed costs make direct-seeding risky and expensive, as is the case with seedless watermelons. Most watermelon growers purchase plants from plant growing experts who may arrange for transport to the field location.

For triploid seedless watermelon production, fruit set and enlargement is dependent upon growth regulators from the pollen grains and from embryos in developing seeds within the fruit. Inadequate pollination results in triploid watermelon fruit that are triangular in shape and of poor quality. Inadequate pollination may increase the incidence of hollowheart. Triploid watermelon flowers do not produce sufficient viable pollen to induce fruit set and development. Therefore, pollen from a normal diploid seeded watermelon variety must be provided. Planting the diploid pollenizer variety in the outside row of the field and then every third row is recommended. As an alternative, the pollenizer variety has been planted every third plant in each row but this makes harvesting of the triploid fruit difficult because mixed diploid and triploid fruit must be separated. This also makes planting difficult because blanks must be left where the diploid should go. Maintaining the rotation of three triploid to one diploid is not easily accomplished.

Currently, it is important to use a diploid pollenizer variety that is marketable because between one-quarter to one-half of all watermelons produced in the field will be of this variety. The rind pattern and/or shape of the seeded pollenizer fruit should be distinguished easily from that of the triploid fruit to reduce confusion at harvest.

It is important that pollen from the diploid pollenizer variety is available when female blossoms on the triploid plants are open and ready for pollination. If planted too early, the diploid variety can set fruit and stop producing male blossoms while the triploid variety is still producing many female blossoms. If planted too late, the triploid will be ready to set fruit but not enough pollen will be ready to provide fruit set.

Watermelon plants develop several vigorous and far-reaching vines, thus requiring large amounts of space for optimum growth and fruit development. Watermelons have been seeded with about two to about four feet between plants in rows about six to about 15 feet apart. This wide spacing requires larger field sizes. Also, the wide spacing provided less interplant competition for water. Cultural practices such as irrigation and polyethylene mulch have led to the use of higher plant populations. Row spacing of 6–8 feet apart and plant spacing of 2–4 feet are common. Often, with close plant spacing, the individual plant sets fewer fruits, which still reach normal size.

Watermelon plants usually have separate male and female flowers but sometimes produce perfect flowers. To achieve fruit set, pollen from the male flower must be transferred to a female flower on that plant or another plant in the field. This pollen transfer is accomplished by several naturally occurring insects, but most effectively by the honeybee. Poor or ineffective pollination of watermelons results in bottle-neck fruits of long-fruited watermelon varieties. In round-fruited varieties, poorly pollinated fruits can be flat-sided or misshapen.

Watermelon has small flowers. Flowering begins about 8 weeks after seeding. Flowers of watermelon are staminate (male), perfect (hermaphroditic), or pistillate (female), usually borne in that order on the plant as it grows. Monecious types are most common, but there are andromonoecious (staminate and perfect) types, mainly the older varieties or accessions collected from the wild. In many varieties, the pistillate or perfect flowers are borne at every seventh node, with staminate flowers at the intervening nodes. The flower ratio of typical watermelon varieties is 7 staminate to 1 pistillate, but the ratio ranges from 4:1 to 15:1.

Watermelon is the only economically important cucurbit with pinnatifid (lobed) leaves; all of the other species have whole (nonlobed) leaves. The leaves are pinnately divided into three or four pairs of lobes, except for an entire-leaf (nonlobed) gene mutant controlled by the nl (nonlobed) gene. Watermelon growth habit is a trailing vine. The stems are thin, hairy, angular, grooved, and have branched tendrils at each node. The stems are highly branched and up to 30 feet long, although there are dwarf types (dw-1 and dw-2 genes) with shorter, less-branched stems. Roots are extensive but shallow, with a taproot and many lateral roots.

Vine length of watermelon varies from dwarf to long. For example, 'Charleston Gray' and 'Jubilee', large-fruited varieties, have vines up to 30 feet long. Short or medium length vines are well suited to varieties with small or medium sized fruit. For example, 'Sugar Baby', 'New Hampshire Midget', and 'Petite Sweet' are short vined, having vine lengths of between about six to about 12 feet and 'Crimson Sweet' has intermediate vine length.

Dwarf mutants have been discovered in watermelon. Two genes cause dwarfing when they are in homozygous recessive condition: dw-1 and dw-2. 'Kengarden' has the genotype dw-1 dw-2. Another gene mutant (Japanese Dwarf, dw-2 dw-2) has increased branching from the crown.

Fruit size is an important consideration in a breeding program since there are different market requirements for particular groups of shippers and consumers. The general categories are: icebox (<12 lb), small, sometimes called pee-wee (12–18 lb), medium (18–24 lb), large (24–32 lb), and giant (>32 lb). Fruit size is inherited in polygenic fashion, with an estimated 25 genes involved. Shippers in the United States work with particular weight categories, such as 18–24 lb for seeded and 14–18 lb for seedless.

In the production of triploid seedless hybrids, currently from one-quarter to one-half of the field has to be planted to a diploid seeded variety. Therefore, higher yield of seedless watermelon per acre could be obtained by using a more efficient pollenizer that would allow more of the field to be planted to the triploid variety.

In theory, seedless triploid hybrids should provide higher yield than diploid hybrids because no energy is used in seed production. However, in practice this may not be the case. Fruit production in triploids is limited by the availability of viable pollen to induce fruit set. Pollination problems are responsible for improper fruit development. It is necessary for all three lobes of the stigma to be fully pollinated if the fruit is to develop fully, and without curvature. In the case of triploid hybrids, it is necessary to have up to one third of the field planted to a diploid pollenizer to assure adequate fruit development in the triploids which are male sterile.

Seedless triploid varieties are produced by crossing a tetraploid (2n=4x=44 chromosomes) inbred line as the female parent with a diploid (2n=2x=22) inbred line as the male parent of the hybrid. The reciprocal cross (diploid female parent) does not produce seeds. The resulting hybrid is a triploid (2n=3x=33). Triploid plants have three sets of chromosomes, and three sets cannot be divided evenly during meiosis. This results in nonfunctional female and male gametes although the flowers appear normal. Since the triploid hybrid is female sterile, the fruit induced by pollination tend to be seedless. Unfortunately, the triploid has no viable pollen, so it is necessary to plant a diploid variety in the production field to provide the pollen that stimulates fruit to form. Usually, one third of the plants in the field are diploid and two thirds are triploid, although production has been observed with as little as 20% diploids. Varieties should be chosen that could be distinguished easily so the seeded diploid fruit can be separated from the seedless triploid fruit for harvesting and marketing.

Most of the tetraploid lines being used by the seed industry have gray rind so that, when crossed with a diploid line with striped rind, it will be easy to separate self-pollinated progeny (which will be seeded fruit from the female parent line) from cross-pollinated progeny (which will be seedless fruit from the triploid hybrid). The grower may discard the gray fruit so they are not marketed as seedless watermelons by mistake. For example, if there is 4% of the fruit from the inbred parent then 4% of total fruits will be unmarketable and reduces marketable yield.

The disclosed method increases the productivity and efficiency of triploid seedless watermelons.

SUMMARY OF THE INVENTION

The present invention relates to a novel method of producing triploid watermelon by using short vine pollinators which are either transplanted or seeded into the row. The present invention also relates to a watermelon plant, and a watermelon variety which have short vines. Specifically, in one preferred embodiment the claimed invention involves the following steps:
1) planting triploid plants and diploid short vine pollinator plants in one or more rows;
2) allowing said plants to mature and develop fruit; and
3) harvesting said fruit.

DEFINITIONS

In the description and tables which follow, a number of terms are used. In order to provide a clear and consistent understanding of the specification and claims, including the scope to be given such terms, the following definitions are provided:

Short vine. As used herein, "short vine" means a watermelon plant having an average internode length of less than three inches and/or a plant diameter of less than six feet.

Average internode length. As used herein the term "average internode length" means the average length of the internodes of a plant genotype measured in inches.

Lobed leaf. As used herein the term "lobed leaf" means a leaf having two or more lobes.

Nonlobed leaf. As used herein the term "nonlobed leaf" means a leaf that is not lobed.

Yield. As used herein, the term "yield" means the total weight in pounds of all seedless watermelon fruit harvested per acre.

Plant. As used herein, the term "plant" includes plant cells, plant protoplasts, plant cells of tissue culture from which watermelon plants can be regenerated, plant calli, plant clumps and plant cells that are intact in plants or parts of plants such as pollen, flowers, seed, leaves, stems and the like.

Quantitative Trait Loci (QTL). As used herein, the term "quantitative trait loci (QTL)" refer to genetic loci that control to some degree numerically representable traits that are usually continuously distributed.

Regeneration. Regeneration refers to the development of a plant from tissue culture.

Plant diameter. As used herein, the term "plant diameter" means the average length of a plant measured in inches.

Single Gene Converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Vine length. As used herein, the term "vine length" is the length of the runners (vines) and is measured in inches.

Short vine diploid pollinator. As used herein, the term "short vine diploid pollinator" means a diploid variety that has a plant diameter of less than six feet and/or an average internode length of less than 3 inches.

Average length of longest runner. As used herein, the term "average length of longest runner" means the average length of the longest runner of the watermelon plant in inches.

Triploid plants. As used herein, "triploid plants" means plants or transplants derived from planting triploid seeds or from micropropagation.

Diploid plants. As used herein, "diploid plants" means plants or transplants derived from planting diploid seeds or from micropropagation.

DETAILED DESCRIPTION OF THE INVENTION

The present invention relates to a novel method of producing triploid watermelon which involves the use of short vine diploid pollinators. The present invention also relates to a watermelon plant, a watermelon variety and a watermelon hybrid which has the short vine characteristics.

The present invention is a novel method which uses a diploid pollinator that takes less space in the field and reduces the total usage of water and fertilizer by diploid plants in a field. This novel method allows the triploid hybrid to produce higher yields due in part to having more space, water, sunlight and nutrients available for the triploid plants and also due to having additional triploid plants per field. The use of this novel short vine diploid pollinator also allows easier harvesting of the triploid fruits produced, since the diploid fruits remain in, or adjacent to, the row where planted and are therefore not in the way and allow easier manual or mechanical harvesting.

Use of a short vine pollinator allows the grower to manage the water, fertilizer and field regimes totally based on the needs of the triploid plants and not managed based on the diploid plants in the field.

In one embodiment of the present invention, transplants of the diploid short vine pollinator seed and transplants of the triploid seed are planted in each row. In a preferred embodiment, a higher number of triploid transplants are planted per field than conventional methods. For example, at a specific field and location, currently the grower plants a total of 2,000 transplants per acre and the field contains both diploid (around 25%–33%) and triploid genotypes (around 67%–75%). In one preferred method of the present invention, the grower establishes approximately 2,000 plants of the triploid and then plants about 400 to about 1,200 plants of the short vine diploid. The short vine diploid plant of the present invention is small and therefore does not require additional space in the row. In comparison, with current production methods, the grower is planting on the average approximately 1,333 triploid transplants and 667 diploid transplants per acre. Whereas, with the method of the present invention, 2,000 triploid plants and about 400–1,200 diploid plants are planted, resulting in an increase of 33% to 50% more triploid plants per acre. These additional triploid plants produce a significant increase in total triploid fruit yield per acre.

In another embodiment of the present invention, the diploid short vine pollinator seed is mixed with the triploid seed prior to planting. In a preferred embodiment, a higher number of triploid seeds are planted per field. For example, at a specific field and location, if the grower plants a total of 2,000 seeds per acre the field will contain both diploid (around 25%–33%) and triploid genotypes (around 67%–75%). In one preferred method of the present invention, the grower would plant 2,000 seeds of the triploid and in addition 200 seeds of the short vine diploid. The short vine diploid plant of the present invention is small and does not require additional space in the row. Therefore in this example, with current methods the grower is planting approximately 1,333 triploid seeds and 667 diploid seeds per acre. Advantageously, with the method of the present invention, 2,000 triploid seeds and 200 diploid seeds are planted, resulting in 66% more triploid plants per acre, which produces a significant increase in yield per acre.

The established plants in a field can be developed from the following methods: 1) planting seeds or any portions of seed; 2) primed or coated seed, or any portions of the seed; 3) plants, or portions thereof, derived from tissue culture or cell culture; 4) cuttings; and 5) planting transplants into the field.

The triploid and diploid seeds can be mixed prior to planting and then sowed or the triploid seed can first be planted, followed by planting the diploid seed or vice versa, depending on expected pollination dates.

The method of the present invention had the unexpected result of providing a good pollen source without having the disadvantages of longer vined diploid pollinators varieties.

The present invention also completely eliminates the need for the current planting procedure of having one row of diploid plants alternated with every two rows of triploid plants.

Other advantages of the present invention include the diploid pollinator is easy to see and avoid stepping on when harvesting. The diploid pollinator is close to the row and therefore should be easy to avoid when picking triploid fruits.

EXAMPLES

The present invention is further detailed in the following Examples, which are offered by way of illustration and are not intended to limit the invention in any manner. Standard techniques well known in the art or the techniques specifically described are utilized.

Example 1

Short Vine Diploid Pollinators

Sixty-nine diploid lines of the short vine plant habit type have been developed. Sixteen lines are shown in Table 1. Of these 16 lines in Table 1, there are 4 different rind pattern types including gray, dark green, light green with narrow stripes, and light green with wide stripes. Also included are lines having: 1) both red and yellow fleshed lines; 2) round, blocky and elongated fruit shapes and 3) lobed and nonlobed leaf types.

These diploid short vine lines can be crossed with many other genetic backgrounds to select for additional short vine lines.

TABLE 1

Short Vine Pollinator

| Number/ID | Rind Pattern | Flesh Color | Fruit Shape | Lobed or Non-lobed |
|---|---|---|---|---|
| 6753 | Gray | Red | Round | Lobed |
| 6741 | Gray | Red | Round | Non-lobed |
| 4935 | Gray | Red | Blocky | Non-lobed |
| 4963 | Gray | Red | Elongated | Lobed |
| 4923 | Dark Green | Red | Round | Lobed |
| 4922 | Dark Green | Red | Round | Non-lobed |
| 4959 | Dk. mottled stripe | Red | Round | Lobed |
| 4915 | Dk. mottled stripe | Red | Round | Non-lobed |
| 4961 | Dk. mottled stripe | Red | Blocky | Lobed |
| 4962 | Dk. mottled stripe | Red | Blocky | Non-lobed |
| 4956 | Dk. mottled stripe | Red | Long | Lobed |
| 4957 | Dk. mottled stripe | Red | Long | Non-lobed |
| 4905 | Tiger stripe | Red | Round | Non-lobed |
| 4932 | Tiger stripe | Red | Blocky | Lobed |

TABLE 1-continued

Short Vine Pollinator

| Number/ID | Rind Pattern | Flesh Color | Fruit Shape | Lobed or Non-lobed |
|---|---|---|---|---|
| 4941 | Tiger stripe | Red | Round | Lobed |
| 4937 | Gray | Yellow | Round | Non-lobed |

Example 2

Short vine diploid lines 6741 and 6754 have been tested as pollinators of triploid plants under field conditions. During 2001, at five different locations in Florida, Georgia and South Carolina, plantings were made using either alternate rows for the pollinator or with the pollinator planted in the same row as the triploid plants. The short vine diploid pollinator induced triploid fruit set earlier, approximately 10 days earlier, when planted in the same row as compared to planting the diploid plants in separate alternate rows from the triploid plants. The quantity of fruit set by the triploid plants was normal and similar in number and size to the standard long vine pollinator. Line 6741 produced more triploid fruit which set earlier than the 6754 line.

Example 3

In 2001, a location near Gilroy, Calif. was planted and harvested where the short vine pollinator was planted at different intervals between the triploid plants down the same row including at the intervals of (every 2, 3, 4, 5 triploid plants). Fruit set decreased at a spacing of one pollinator every 4 or 5 plants but fruit set was normal using short vine pollinators for every 2 or 3 triploid plants compared to long vine pollinators.

Example 4

Line 6741

The watermelon diploid line 6741 of the present invention have the characteristics of a short vine and results in a significant increase in triploid fruit production when used as a short vine pollinator for triploid hybrid production. Using 6741 as a pollinator provides a great benefit because it results in easier harvest and reduced occurrence of undesirable diploid fruit, which when harvested must be kept separate from the seedless triploid watermelon. Additionally, the use of 6741 as pollinator results in the yield of the triploid watermelon of the present invention is increased substantially.

In the development of line 6741, 'Sugar Bush' was crossed with 'Mickylee' in 1986 and selfed for 4 generations. A selection was then crossed with line 'B25' in 1991 and selected for non-lobed, short vine and light green rind with no stripes.

Trait characteristics of watermelon line 6741 are listed below:
    MATURITY: 80 days (a little earlier than main season/avg)
    FRUIT: Rind is light green with faint mottling and no stripes; flesh is red
    SIZE: Diameter—8 inches
    Length—9 inches
    Rind—⅝ inch Example 5

Line 6754

The watermelon diploid line 6754 of the present invention have the characteristics of a short vine and results in a significant increase in fruit production when used as a short vine pollinator for triploid hybrid production. Using 6754 as a pollinator provides a great benefit because it results in easier harvest and reduced occurrence of undesirable diploid fruit which when harvested must be kept separate from the seedless triploid watermelon. Additionally, the use of 6754 as a pollinator results in the yield of the triploid watermelon of the present invention is increased substantially.

Trait characteristics of watermelon line 6754 are listed below:
    MATURITY: 80 days
    FRUIT: Rind—Light green with faint mottling and no stripes; flesh—red
    SIZE: Diameter—8 inches
    Length—9 inches
    Rind—⅝ inch This invention is also directed to methods for producing a seedless triploid watermelon fruit by using short vine diploid pollinators.

As used herein, the term "plant" includes plant cells, plant protoplasts, plant cell of tissue culture from which watermelon plants can be regenerated, plant calli, plant clumps, and plant cells that are intact in plants or parts of plants, such as pollen, flowers, leaves, rind, flesh and the like.

When the term inbred watermelon plant is used in the context of the present invention, this also includes any single gene conversions of that inbred. The term single gene converted plant as used herein refers to those watermelon plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental watermelon plants for that inbred. The parental watermelon plant which contributes the gene for the desired characteristic is termed the nonrecurrent or donor parent. This terminology refers to the fact that the nonrecurrent parent is used one time in the backcross protocol and therefore does not recur. In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a watermelon plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

A further aspect of the invention relates to tissue culture of watermelon plants designated N3C13. As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, leaves, roots, root tips, anthers, and the like. In a preferred embodiment, tissue culture is embryos, protoplast, meristematic cells, pollen, leaves or anthers. Means for preparing and maintaining plant tissue culture are well known in the art. By way of example, a tissue culture comprising organs such as anthers, has been used to produce regenerated plants. (See U.S. Pat. Nos. 5,445,961; 5,322,789; 5,948,957 and 5,969,212, the disclosures of which are incorporated herein by reference).

Deposit Statement

Applicant has made a deposit of at least 2500 seeds of watermelon line 6741 with the American Type Culture Collection (ATCC), Manassas, Va., 20110-2209 U.S.A., ATCC Accession Number No: PTA-4027. During pendency of this application, access to the invention will be afforded to the Commissioner by request; all restrictions upon availability to the public will be irrevocably revoked upon granting of the patent; the deposit of line 6741 will be maintained in the ATCC depository, which is a public depository, for a period of 30 years, or 5 years after the most recent request, or for the effective life of the patent, whichever is longer, and will be replaced if it becomes nonviable during that period. The viability of the seeds was tested at the time of deposit. Applicant has satisfied all the requirements of 37 C.F.R. §§1.801–1.809. Applicant imposes no restrictions on the availability of the deposited material from the ATCC; however, Applicant has no authority to waive any restrictions imposed by law on the transfer of biological material or its transportation in commerce. Applicant does not waive any infringement of its rights granted under this patent or under the Plant Variety Protection Act (7 USC 2321 et seq.).

Although the foregoing invention has been described in some detail by way of illustration and example for purposes of clarity and understanding. However, it will be obvious that certain changes and modifications such as single gene modifications and mutations, somoclonal variants, variant individuals selected from large populations of the plants of the instant inbred and the like may be practiced within the scope of the invention, as limited only by the scope of the appended claims.

What is claimed is:

1. A diploid short vine watermelon pollinator line designated 6741, a sample of said seed having been deposited under ATCC Accession No. PTA-4027.

2. A seed of diploid short vine watermelon pollinator line designated 6741, a sample of said seed having been deposited under ATCC Accession No. PTA-4027.

3. A watermelon plant, or a part therefore, produced by growing the seed of claim 2.

4. Pollen of the plant of claim 3.

5. An ovule of the plant of claim 3.

6. A method for producing a hybrid watermelon seed comprising crossing a first parent watermelon plant with a second parent watermelon plant and harvesting the resultant hybrid watermelon seed, wherein said first or second parent watermelon plant is the watermelon plant of claim 3.

7. A method for developing a watermelon plant in a watermelon plant breeding program using plant breeding techniques which include a watermelon plant, or its parts, as a source of plant breeding material comprising: crossing the watermelon plant of claim 3 with a different watermelon plant and wherein said plant breeding techniques are selected from the group consisting of recurrent selection, backcrossing, pedigree breeding, mass selection, restriction fragment length polymorphism enhanced selection, genetic marker enhanced selection, and transformation.

* * * * *